Patent Number: 4,825,702
Date of Patent: May 2, 1989

United States Patent [19]
Cizek

[54] YARN TESTING METHOD

[75] Inventor: Jaromir Cizek, Port Elizabeth, South Africa

[73] Assignee: South African Inventions Development Corporation, Transvaal, South Africa

[21] Appl. No.: 34,509

[22] Filed: Apr. 6, 1987

[30] Foreign Application Priority Data

Apr. 15, 1986 [ZA] South Africa .............. 86/2796

[51] Int. Cl.⁴ .............................................. G01N 3/08
[52] U.S. Cl. ............................................ 73/828; 73/834
[58] Field of Search ................ 73/160, 828, 830, 831, 73/833, 834, 860, 856

[56] References Cited

U.S. PATENT DOCUMENTS

| | | | |
|---|---|---|---|
| 2,533,332 | 12/1950 | Steiding | 73/160 |
| 3,049,916 | 8/1962 | Weiner | 73/828 |
| 3,209,589 | 10/1965 | Schlatter | 73/160 |
| 3,287,964 | 11/1966 | Dennis et al. | 73/160 |
| 3,533,284 | 10/1970 | Slemmons et al. | 73/160 |
| 3,885,417 | 5/1975 | Stern | 73/160 |
| 3,992,936 | 11/1976 | Clemens et al. | 73/160 |
| 4,100,796 | 7/1978 | Gayler et al. | 73/160 |
| 4,173,787 | 11/1979 | Katuna et al. | 73/160 |
| 4,245,512 | 1/1981 | Saunders | 73/828 |

FOREIGN PATENT DOCUMENTS

| | | | |
|---|---|---|---|
| 775849 | 1/1968 | Canada | 73/160 |
| 1124268 | 2/1962 | Fed. Rep. of Germany | 73/160 |
| 2105302 | 10/1971 | Fed. Rep. of Germany | 73/160 |

Primary Examiner—Stewart J. Levy
Assistant Examiner—Robert R. Raevis
Attorney, Agent, or Firm—Nixon & Vanderhye

[57] ABSTRACT

The invention provides a method of testing yarn comprising periodically feeding a length of yarn by means of a fluid stream along a pathway so that it extends between a pair of spaced clamps, clamping the length of yarn towards the ends thereof by means of the clamps and causing one or both clamps to move relative to the other progressively to tension the yarn until breakage. Tension and elongation of the yarn is measured.

19 Claims, 7 Drawing Sheets

YARN TESTING METHOD

FIELD OF THE INVENTION

This invention relates to a method of testing yarn and apparatus adapted for use in the method.

BACKGROUND OF THE INVENTION

The method of the invention will in particular be suitable for determining the suitability of yarns for weaving and knitting purposes. It is however envisaged that the method of the invention could find other applications and the term "yarn" herein includes any elongated fibre, strand, string, sliver or the like. The method of the invention envisages determining the tensile properties of a yarn and could also give a satistical indication of the number of weak points per unit length of yarn.

SUMMARY OF THE INVENTION

According to the invention the method of testing a yarn is characterized in the steps of feeding a length of yarn so that it extends between a pair of spaced clamps, clamping the length of yarn towards the ends thereof by means of the clamps, and causing one or both clamps to move relative to the other progressively to tension the yarn.

Further according to the invention the method includes the step of measuring the yarn tension during the tensioning process.

Still further according to the invention the method includes the step of measuring the elongation of the length of yarn between the clamps during the tensioning process. In one embodiment of the invention the yarn will be tensioned until breakage thereof and in such an arrangement, the invention envisages that a measurement will be made of the elongation of the yarn until breakage occurs.

Also according to the invention the tension in the yarn is measured by causing the yarn to engage a sensor with the yarn displaced out of a linear path between the clamps. It is for example envisaged that the yarn should be caused to follow a generally half-wave pathway with the sensor disposed at the wave crest.

The elongation of the yarn during the tensioning process is preferably measured by measuring the distance which the clamps, move relative to one another.

Still further according to the invention one or both clamps will be in the nature of a rotatable disc or pulley having a belt draped over portion of the periphery thereof, and the method includes the step of clamping the yarn between the disc and belt, by rotating the disc and the belt and feeding the yarn into the nip between the belt and disc. With such an arrangement, the step of causing relative movement between the clamps can be carried out by continuing to rotate at least one of the discs once the yarn has been clamped, with the rotational axis of the disc being disposed transverse to the direction of the yarn.

Also according to the invention the yarn is fed along a pathway extending between the clamps from a reservoir and the method includes the steps of periodically opening such pathway to permit yarn to be fed so that it extends between the clamps. Where the clamps are in the form of discs it is envisaged that a clamp will intersect the yarn pathway with one or more apertures in the disc being adapted to align with the pathway to open the latter periodically upon rotation of the disc.

Still further according to the invention the method is characterized in feeding the yarn by means of a fluid stream. The method of the invention envisages that a length of yarn will be accumulated during the tensioning process preparatory to being fed to the clamp during the feeding cycle. With this arrangement continuous yarn feed is possible, with means being provided to take up slack in the yarn being prepared for feeding to the clamp in a controlled fashion while a preceding length is being tensioned.

Also included within the scope of the invention is apparatus adapted for use in the method, comprising a pair of spaced clamps, means for feeding a length of yarn into a position for clamping by the clamps, the arrangement being one wherein one or both clamps are movable relative to the other in order to tension a clamped length of yarn.

Still further according to this aspect of the invention, a sensor is provided intermediate the clamps to measure the yarn tension during relative movement between the clamps. It is envisaged that such a sensor could be in the nature of a force transducer displaced out of a linear path between the clamps. For example the yarn could be guided to follow a U-shaped path between a first guide, the sensor, and a second guide.

Also according to the invention one or both clamps comprise a disc or pulley with an endless belt engaging over portion of the periphery thereof, so that the yarn fed into the nip between the disc and belt upon rotation of the former, will be clamped between the periphery of the disc and the belt. The invention envisages that the rotational axis of the disc will be disposed transverse to the direction of the yarn so that after clamping further rotation of the disc will act to tension the yarn.

Also according to the invention the feed means comprises a fluid stream and pathway therefore, with the clamps and sensor being disposed within such pathway. It is a feature of the invention that means will be provided for periodically opening the pathway to permit yarn to be fed therealong. Such means may comprise a rotatable disc which intersects the pathway and which defines one or more apertures therein, with such apertures being adapted to align with the pathway to open the latter periodically upon rotation of the disc. It is envisaged that the disc could form part of a clamp of the apparatus. Preferably the feed means will also include a continuous yarn feed device which is adapted to introduce a predetermined length of yarn into the feed pathway at the onset of each clamping and tensioning cycle. Such a feed device could for example comprise a pair of feed rollers rotating at a predetermined speed, with the feed pathway being adapted to be opened periodically to draw yarn from the feed rollers into the pathway. It is envisaged that prior to opening the pathway, a predetermined length of yarn will be accumulated as a result of feed from the rollers, with an eccentric device being provided to take up slack in a controlled fashion when the pathway is closed. The invention provides that the eccentric will move from a position proximate to the feed rollers to a remote position to take up the slack.

Still further according to the invention means is provided for measuring the elongation of the yarn during the tensioning process. The invention envisages that such means could comprise means for measuring the angular displacement of a disc clamp during the tensioning process until breakage of the yarn occurs.

DESCRIPTION OF THE DRAWINGS

In order to more clearly to illustrate the invention, an embodiment thereof will now be described by way of example, with reference to the accompanying drawings wherein.

DETAILED DESCRIPTION OF THE INVENTION

Figure 6:
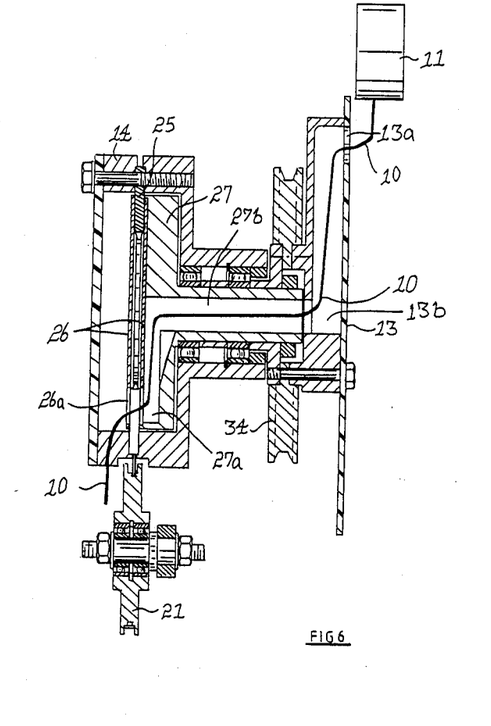
FIG. 6 is an enlarged view of a section on line VI—VI in FIG. 4.
Figure 7:
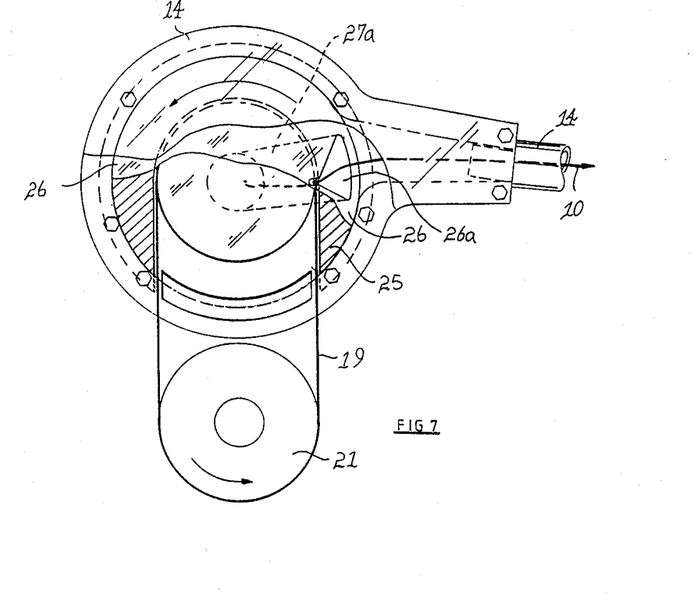
FIG. 7 is an enlarged partially sectioned elevation of portion of the apparatus in FIG. 4.

Referring to the drawings the apparatus in accordance with the invention for testing yarn 10 comprises a yarn pathway which starts with a spool 12 or other suitable reservoir for yarn, and which terminates in an outlet 16 which is coupled to a suction device, not shown. The yarn 10 is continually fed from the spool 12 by means of a pair of rollers 11 and during a feed cycle, a predetermined length of yarn which has passed through the rollers 11, is sucked along the yarn pathway to be tested during a testing cycle which is described in more detail below. In order to prevent knotting of the yarn during the feed cycle, an eccentric device is provided to guide the yarn from a position remote from the feed rollers 11 towards a position which proximates the rollers 11 and thus serves to take up slack during the feed cycle. With reference to FIG. 6 it will be noted that the eccentric comprises a plate 13 which has an eccentric aperture 13a therein which defines an inlet to the suction pathway 13b for the yarn.

Figure 4:
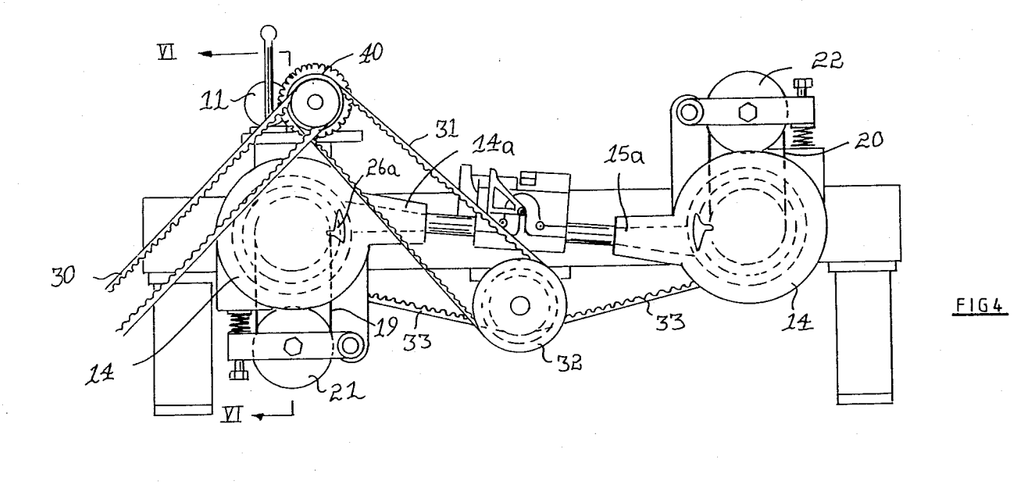
FIG. 4 is an elevation of apparatus in accordance with the invention.
Figure 5:
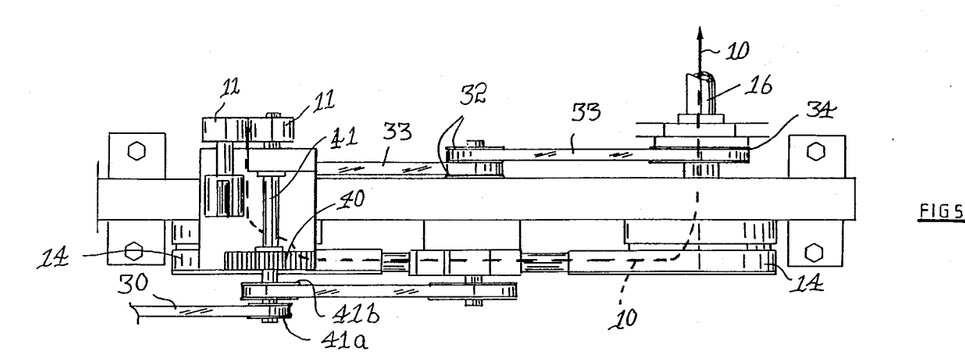
FIG. 5 is a plan of the apparatus in FIG. 4.

The yarn pathway 13b leads to a pair of spaced clamps in the form of pulleys 17 and 18 over which belts 19 and 20 respectively run. The belts 19 and 20 are of the endless variety and extend between the pulleys 17 and 18 and spaced idlers 21 and 22 respectively. During the testing cycles mentioned above, yarn is fed into the nip defined by the belts 19, 20 and the pulleys 17, 18, and thus clamped. During further rotation of the pulleys 17 and 18 in the direction shown in FIG. 1, the yarn is tensioned until breakage occurs. During the tensioning stage the tension in the yarn 10 is measured by a force transducer 23 which is located in the yarn pathway. In the zone of the force transducer 23, the yarn pathway follows a half-wave curve with the yarn passing around a roller 22 over the transducer 23 and back around a roller 24. During the tensioning process, the elongation in the yarn 10 will also be measured by means of a slotted pulse generator 40, FIG. 4, 5, which is coupled in the drive train for the apparatus. By counting the number of pulses given by the generator 40 during the period when the force measured by the transducer 23 is greater than zero, the elongation of the yarn can be determined.

Figure 1:
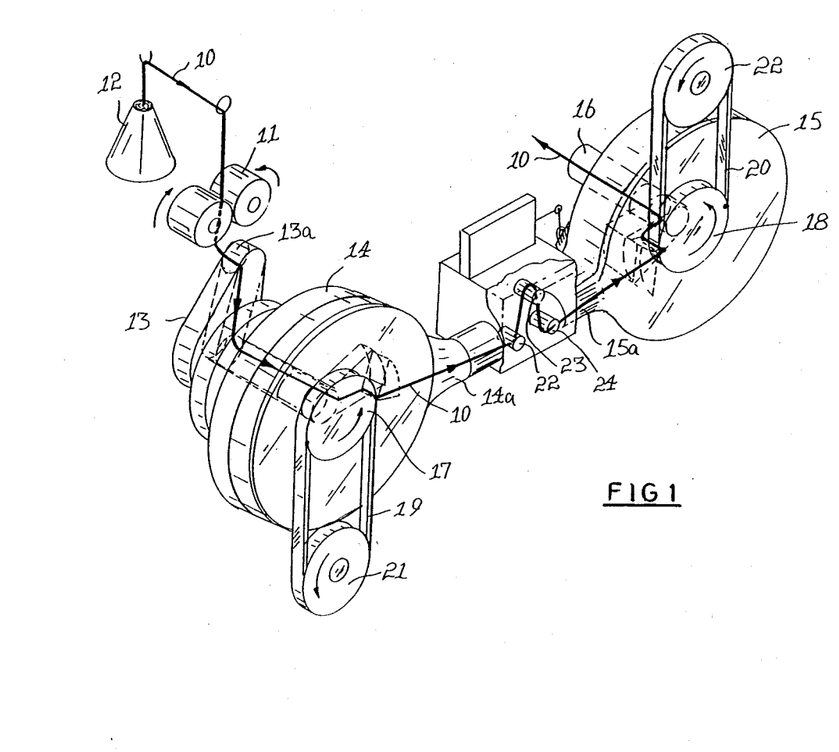
FIG. 1 is a schematic illustration of the yarn pathway through the apparatus in accordance with the invention.
Figure 2:
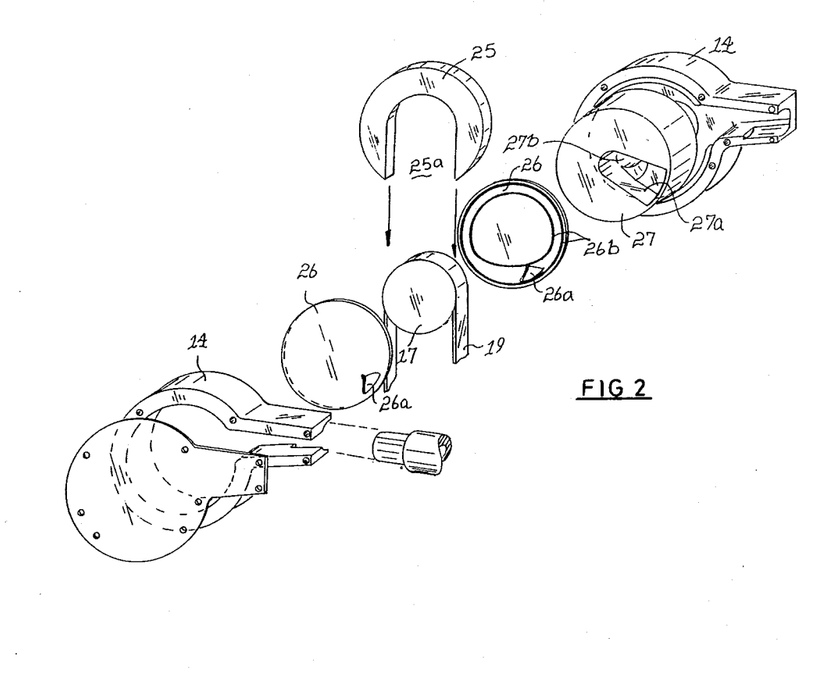
FIG. 2 is an exploded view of portion of the pathway in FIG. 1.
Figure 3:
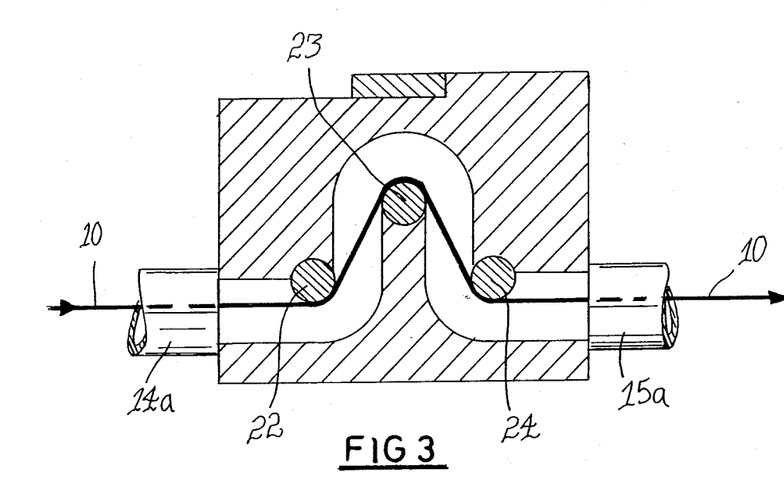
FIG. 3 is a sectioned elevation of a force transducer in the pathway in FIG. 1.

The clamping and tensioning pulleys 17 and 18 are located in spaced housings 14 and 15, which define an outlet 14a and an inlet 15a respectively, the outlet 14a and inlet 15a being coupled in the pathway leading to and from force transducer zone, FIG. 1. Also rotatable within the housing 14 in conjunction with the pulley 17, is a disc 27 which defines an axial portion 27b which extends from the portion 13b of the yarn pathway described above. From the axial portion 27b, the yarn pathway extends radially along a cut-out 27a in the disc 27 to beyond the periphery of a pulley 17. At the outer extremity of the cut-out 27a, the latter aligns with apertures 26a in a pair of plate elements 26 which flank the pulley 17 and rotate in conjunction therewith (The elements 26, pulley 27 and disc 27 are joined together by any suitable fastening device, such as a bolt or glue). A horse-shoe shaped disc 25 fits between the plates 26 and defines a cut-out 25a therein so that the plate 25 seals off the apertures 26a in all angular positions of the plates 26 except when the apertures 26a align with the cut-out 25a. Thus, during the period when the apertures 26a align with the cut-out 25a, the yarn pathway will be opened and yarn will be sucked therealong by means of the suction device. With reference to FIG. 2 it will be noted that the cut-out 25a corresponds with a 180° portion of the pulley 17 which is not in engagement with the belt 19. The feeding and suction cycle thus commences when the pulley 17 and belt 19 release a length of yarn, and the cycle ceases, when the belt and pulley again clamp a length of yarn at the onset of a tensioning cycle. With this arrangement, suction at the outlet 16 will be continuous, with suitable seals such as that shown at 26b on the plates 26 being provided effectively to shut-off airflow during the tensioning cycle.

As mentioned above the disc 27, pulley 17, plates 26, an eccentric plate 13, will all rotate in conjunction and for this purpose a common drive pulley 34, FIG. 6, is provided. The drive train of the apparatus is shown more clearly in FIG. 4 and FIG. 5, and comprises a belt 30 driven by a suitable drive motor, not shown. The belt 30 drives a shaft 41 via a pulley 41a, with the shaft 41 driving the pulse generator 40, feedrollers 11, and a pulley 41b. The latter pulley in turn drives a pulley 32 which drives a belt 33 which in turn drives pulleys 34 for appropriate rotation of the clamping pulleys 17 and 18.

The advantages of the arrangement of the invention will be apparent to persons skilled in the art. The apparatus provides a continuous yarn feed with extremely rapid threading and tensioning of the yarn to breakage. With the arrangement of the invention yarn can be tested at a rapid rate to provide an indication of the level and frequency of weak places in the yarn and therefore the expected weaving performance of the yarn.

Doubtless variations of the invention exist without departing from the principles set out in the consistory clauses.

I claim:

1. A method of testing yarn, comprising the steps of:
   feeding a length of yarn so that it extends along a passage between a pair of spaced clamps;
   clamping the length of yarn towards the ends thereof by means of the clamps;
   causing one or both clamps to move relative to the other during a tensioning cycle, progressively to tension the yarn;
   closing said passage against further feeding of said yarn, said closing being during or after said clamping, said passage remaining closed during said tensioning cycle;

causing one or both clamps to move towards one another after said tensioning cycle during a feeding cycle; and opening the passage to permit yarn to move therealong during the feeding cycle.

2. The method according to claim 1, wherein the yarn is tensioned until breakage thereof including the step of measuring the elongation of the length of yarn until such breakage occurs.

3. The method according to claim 1, wherein one or each clamp is in the form of a rotatable pulley having a belt draped over a portion of the periphery thereof and the method comprises the steps of clamping the yarn between the pulley and the belt by rotating the pulley and the belt and feeding the yarn into the nip between the belt and pulley.

4. The method according to claim 3, wherein the tensioning cycle comprises causing relative movement between the clamps by rotating at least one of the pulleys once the yarn has been clamped, with the rotational axis of the pulley being disposed transversely to the longitudinal direction of the clamped yarn.

5. The method according to claim 3, wherein at least one clmap is in the form of, or is associated with, a rotatable disc and said clamp intersects the passage with an aperture in the disc being alignable with the passage to open and close the passage periodically upon rotation of the disc.

6. The method according to claim 1, wherein the yarn is fed by means of a fluid stream when said passage is opened during the feeding cycle.

7. The method according to claim 1, wherein a length of yarn is fed and accumulated in a controlled fashion during said tensioning cycle preparatory to being fed to the clamps during said feeding cycle.

8. A method according to claim 1, wherein said passage is opened at both ends thereof during the feeding cycle to permit yarn to enter said passage from one end thereof while yarn tested in a preceding tensioning cycle is scavenged from the passage through the other end thereof.

9. Apparatus for use in the method as claimed in claim 1, said apparatus comprising:

a pair of spaced clamps;

means for feeding a length of yarn along a passage into position for clamping by the clamps during a feed cycle, one or both clamps being movable relative to the other in order to tension a clamped length of yarn during a tensioning cycle; and gate means for opening said passage at the onset of the feeding cycle to permit yarn to be fed along said passage, and for closing said passage at the onset of said tensioning cycle.

10. Apparatus according to claim 9, and further including a sensor intermediate the clamps for measuring yarn tension during the tensioning cycle, said sensor being between the clamps and disposed intermediate a pair of guide formations, the arrangement being one wherein said yarn is guided to follow a generally U-shaped path between a first guide formation, said sensor and a second guide formation.

11. Apparatus according to claim 9, wherein one or each clamp comprises a pulley with an endless belt engaging over a portion of the periphery thereof, so that yarn fed into the nip between the pulley and the belt upon rotation of the pulley with the belt will be clamped onto the periphery of the pulley.

12. Apparatus according to claim 11, wherein the rotational axis of the pulley is disposed transverse to the longitudinal direction of the clamped yarn so that after clamping, further rotation of the pulley will act to tension the yarn during said tensioning cycle.

13. Apparatus according to claim 9, wherein the feeding means comprises a fluid stream ducted along the passage which extends between the clamps, during the feeding cycle.

14. Apparatus according to claim 9, wherein the gate means comprises a disc which intersects said passage and which defines an aperture therein, said aperture being alignable with said passage periodically upon rotation of said disc, to open said passage.

15. Apparatus according to claim 14, wherein the disc is constituted by, or associated with, a clamp.

16. Apparatus according to claim 14, wherein the feeding means includes a continuous yarn feed device for introducing a predetermined length of yarn into said passage at the onset of each feeding cycle.

17. Apparatus according to claim 16, wherein the feeding means comprises a pair of feed rollers rotating at a constant speed, with said passage being openable at the onset of the feeding cycle to draw yarn from the feed rollers into the passage, and further includes an eccentric device for taking up slack of yarn fed by said feed rollers while said passage is closed during the tensioning cycle and for releasing yarn fed by the feed rollers once said passage is opened at the onset of the feeding cycle.

18. Apparatus according to claim 17, wherein the eccentric device is movable from a position proximate to the feed rollers to a position remote from the feed rollers to take up the slack in the yarn when said passage is closed and to return to a position proximate the feed rollers when said passage is opened to release fed yarn to said passage.

19. Apparatus according to claim 9, wherein said gate means is for opening both ends of the passage at the onset of the feeding cycle to permit yarn to be fed along said passage from the one end thereof and to permit yarn tested during a preceding tensioning cycle, to be scavenged from the other end of said passage.

* * * * *